United States Patent [19]
Reynolds et al.

[11] Patent Number: 5,464,945
[45] Date of Patent: Nov. 7, 1995

[54] OLIGONUCLEOTIDE PROBES SPECIFIC FOR THE HUMAN ALPHA SATELLITE LOCUS

[75] Inventors: Rebecca L. Reynolds, Alameda; P. Sean Walsh, Walnut Creek, both of Calif.

[73] Assignee: Hoffmann-La Roche Inc., Nutley, N.J.

[21] Appl. No.: 938,084

[22] Filed: Aug. 28, 1992

[51] Int. Cl.[6] .............................. C07H 21/04; C12Q 1/68
[52] U.S. Cl. ..................................... 536/24.31; 536/24.33; 435/6; 435/91.2; 935/6; 935/78
[58] Field of Search .......................... 435/6, 91; 536/23.1, 536/24.1, 24.3, 24.31; 935/77, 78

[56] References Cited

U.S. PATENT DOCUMENTS 4,683,202  7/1987  Mullis ........................................ 435/91

OTHER PUBLICATIONS

Waye et al. Biotechniques (1989) 7 (8) 852–855.
Meyne et al. Geomics (1989) 4: 472–478.
Vigilant et al. Proc Natl Acad Sci. USA (1989) 86: 9350–9354.
Vigilant et al. Science (1991) 253:1503–1507.
Gibco BRL Catalog, 1992, "Human DNA Quantitation System".
Whitehead et al., 1983, "Enhanced Luminescence Procedure for Sensitive Determination of Peroxidaselabelled Conjugates in Immunoassay" Nature 305:158–159.
Willard, 1985, "Chromosome–Specific Organization of Human Alpha Satellite DNA" Am. J. Hum. Genet. 37:524–532.
Wayne and Willard, 1986, "Structure, Organization, and Sequence of Alpha Satellite DNA From Human Chromosome 17: Evidence for Evolution by Unequal Crossing–Over and an Ancestral Pentamer Repeat Shared with the Human X Chromosome" Molecular and Cellular Biology 6(9):3156–3165.
Britten et al., 1988, "Sources and Evolution of Human Alu Repeated Sequences" Proc. Natl Acad. Sci. USA 85:4770–4774.
Vigilant et al., 1989, "Mitochondrial DNA Sequences in Single Hairs From a Southern African Population" Proc. Natl. Acad. Sci. USA 86:9350–9354.
Waye et al., 1989, "A Simple and Sensitive Method for Quantifying Human Genomic DNA in Forensic Speciment Extracts" BioTechniques 7(8):852–855.
Stoneking et al., 1991, "Population Variation of Human mtDNA Control Region Sequences Detected by Enzymatic Amplification and Sequence–Specific Oligonucleotide Probes" Am. J. Hum. Genet. 48:370–382.
Klevan et al., 44th Annual Meeting of the American Academy of Forensic Sciences, New Orleans Feb. 17–22, 1992 "Chemiluminescent Quantitation of Human DNA From Biological Samples".

*Primary Examiner*—Margarat Parr
*Assistant Examiner*—Carla Myers
*Attorney, Agent, or Firm*—George M. Gould; Dennis P. Tramaloni; Stacey R. Sias

[57] ABSTRACT

The present invention provides methods and reagents for the estimation of the quantity of human DNA contained in a sample. Immobilized sample DNA is hybridized to a biotinylated oligonucleotide probe that hybridizes to a human genomic or mitochondria DNA sequence. The subsequent binding of streptavidin-horseradish peroxidase to the bound probe allows for chemiluminescent detection using a luminol-based reagent and X-ray film. In addition, the present invention provides methods and reagents to assess the quality of DNA contained in a sample. The sample is first size fractionated by agarose gel electrophoresis, and then immobilized, hybridized to a biotinylated oligonucleotide probe, and detected using the chemiluminescent method as used in the quantity estimation methods of the present invention.

4 Claims, 2 Drawing Sheets

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

TAGAAGCATT CTCAGAAACT ACTTTGTGAT GATTGCATTC     40

( 2 ) INFORMATION FOR SEQ ID NO:2:

(i) SEQUENCE CHARACTERISTICS:
  (A) LENGTH: 40 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:2:

CACTATTTGT AGAATGTGCA AGTGGATATT TAGGCCTCTC          40

(2) INFORMATION FOR SEQ ID NO:3:

(i) SEQUENCE CHARACTERISTICS:
  (A) LENGTH: 40 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:3:

CAGAAGCATT CTCAGAACCT TCTTCGTGAT GTTTGCATTC          40

(2) INFORMATION FOR SEQ ID NO:4:

(i) SEQUENCE CHARACTERISTICS:
  (A) LENGTH: 130 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:4:

TAGAAGCATT CTCAGAAACT ACTTTGTGAT GATTGCATTC AAGTCACAGA GTTGAACATT          60

CCCTTTGACA GAGCAGTTTG GAAACTCTCT TTGTGTAGAA TCTGCAAGTG GAGATATGGA          120

CCGCTTTAGG          130

(2) INFORMATION FOR SEQ ID NO:5:

(i) SEQUENCE CHARACTERISTICS:
  (A) LENGTH: 131 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:5:

CAGTAGCATT CACAGAAAAC TCTTGGTGAC GACTGAGTTT AACTCACAGA GCTGAACATT          60

CCTTTGGATG GAGCAGTTTC GAAACACACT ATTTGTAGAA TGTGCAAGTG GATATTTAGG          120

CCTCTCTGAG G          131

(2) INFORMATION FOR SEQ ID NO:6:

(i) SEQUENCE CHARACTERISTICS:
  (A) LENGTH: 130 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:6:

CAGAAGCATT CTCAGAACCT TCTTCGTGAT GTTTGCATTC AACTCACAGT GTTGAACCTT          60

```
TCTTTGATAG  TTCAGGTTTG  AAACGGTCTT  TCTGTAGAAA  CTGCAAGTAG  ATATTTGGAC        120

CGCTCTGAGG                                                                    130
```

( 2 ) INFORMATION FOR SEQ ID NO:7:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

```
GAAACTCTCT  TTGTGTAGAA  TCTGCAAGTG  GAGATATGGA                                 40
```

( 2 ) INFORMATION FOR SEQ ID NO:8:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

```
AAGTCACAGA  GTTGAACATT  CCCTTTGACA  GAGCAGTTTG                                 40
```

( 2 ) INFORMATION FOR SEQ ID NO:9:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
TAGAAGCATT  CTCAGAAACT  ACTTTGTGAT  GATTGCATTC  AAGTCACAGA  GTTGAACATT         60
```

( 2 ) INFORMATION FOR SEQ ID NO:10:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

```
TAGAAGCATT  CTCAGAAACT  ACTTTGTGAT  GATTGCATTC  AAGTCACAGA  GTTGAACATT         60

CCCTTTGACA  GAGCAGTTTG                                                         80
```

( 2 ) INFORMATION FOR SEQ ID NO:11:

( i ) SEQUENCE CHARACTERISTICS:
        ( A ) LENGTH: 100 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

```
TAGAAGCATT CTCAGAAACT ACTTTGTGAT GATTGCATTC AAGTCACAGA GTTGAACATT      60

CCCTTTGACA GAGCAGTTTG GAAACTCTCT TTGTGTAGAA                           100
```

( 2 ) INFORMATION FOR SEQ ID NO:12:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

```
GGCGGTATGC ACTTTTAACA GTCACCCCCC AACTAACAC                             39
```

( 2 ) INFORMATION FOR SEQ ID NO:13:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

```
GTCTTTAACT CCACCATTAG CACCCAAAGC TAAGATTCTA                            40
```

( 2 ) INFORMATION FOR SEQ ID NO:14:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

```
CGTGAAATCA ATATCCCGCA CAAGAGTGCT ACTCTCCTCG                            40
```

( 2 ) INFORMATION FOR SEQ ID NO:15:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

```
GAACTGTATC CGACATCTGG TTCCTACTTC AGGGTCATAA AGC                        43
```

( 2 ) INFORMATION FOR SEQ ID NO:16:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

```
GACATCACGA TGGATCACAG GTCTATCACC CTATTAACCA C                          41
```

( 2 ) INFORMATION FOR SEQ ID NO:17:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:17:

CATCCTCCGT GAAATCAATA TCCCGCACAA GAGTGCTAC 39

( 2 ) INFORMATION FOR SEQ ID NO:18:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:18:

GTCTTTAACT CCACCATTAG CACCCAAAGC 30

( 2 ) INFORMATION FOR SEQ ID NO:19:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:19:

CTCCACCATT AGCACCCAAA GCTAAGATTC 30

( 2 ) INFORMATION FOR SEQ ID NO:20:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:20:

GTATCCGACA TCTGGTTCCT ACTTCAGGGT C 31

OLIGONUCLEOTIDE PROBES SPECIFIC FOR THE HUMAN ALPHA SATELLITE LOCUS

FIELD OF THE INVENTION

This invention relates to the process of estimating the quantity and quality of human nuclear and mitochondrial DNA contained in a sample. More specifically, it relates to the use of biotinylated probes that hybridize to a human alpha satellite locus, such as D 17Z1, or to a conserved sequence in the mitochondrial control region and a chemiluminescent detection assay to analyze immobilized DNA. Additionally, it relates to the use of gel electrophoresis followed by Southern Blotting to assess the degradation state of DNA in a sample.

Background of the Invention

An increasingly detailed analysis of human genetic diversity has been made possible by techniques of molecular biology such as amplification of DNA by the polymerase chain reaction (PCR) (Saiki et al., 1988, *Science* 23.9.:487–491, U.S. Pat. Nos. 4,683,195; 4,683,202; and 4,965.188; all of which are incorporated herein by reference) and DNA typing based on restriction fragment length polymorphisms (RFLP) (Jeffereys et al., 1985, *Nature* 314:67–73). The specificity and sensitivity of PCR amplification have resulted in widespread use of that method in the fields of forensic science (Blake et al., 1991, *Journal of Forensic Sciences* 37(3):700–726, incorporated herein by reference), studies of ancient DNA samples (Paabo et al., 1988, *Nucleic Acids Research* 16:9775–9787, incorporated herein by reference), analysis of genetic diseases (Gibbs et al., 1989, in Erlich (ed.), *PCR Technology: Principles and Applications for DNA Amplification*, Stockton Press, New York: 153–169, incorporated herein by reference), and in studies of population genetics (Helmuth et al., 1990, *American Journal of Human Genetics* 47:515–523, incorporated herein by reference).

The field of forensic science, in particular, has been revolutionized by the ability to extract and type DNA from forensic evidence samples (Reynolds et al., 1991, *Analytical Chemistry* 63:1–15, incorporated herein by reference). In forensics, where many biological evidence samples contain either extremely small quantities of DNA or DNA that has been degraded, the quantity and quality of DNA in a sample can be important factors in selecting suitable analytical methods. For example, RFLP-based typing methods require relatively large quantities of undegraded DNA, typically greater than 50 nanograms. Analysis of samples containing only a few nanograms of possibly degraded DNA may require the additional sensitivity and specificity of PCR-based methods. In general, the efficiency of a PCR amplification is influenced by the quantity, quality, and purity of the sample DNA. Because the success of most DNA analysis methods is dependent on the quantity and quality of the DNA sample, it is important to be able to quantitate the DNA and assess the quality of DNA in samples prior to analysis.

Current methods for quantitation of DNA include UV spectroscopy, fluorometry, and semi-quantitation by agarose gel electrophoresis followed by staining with ethidium bromide. However, these methods require multi-nanogram quantities of non-denatured DNA for analysis and are not specific for human DNA. In addition, they do not distinguish between nuclear and mitochondrial DNA. Quantitation methods specific for human DNA are important for the analysis of samples which sometimes contain bacterial or fungal DNA, such as forensic evidence samples, ancient DNA samples, and clinical samples. Recently, Waye et al., 1989, *BioTechniques* 7(8):852–855, incorporated herein by reference, reported a method that is relatively specific for human DNA. However, this method requires a radioactive label and takes several hours to obtain results. There is a need for a rapid, sensitive, and human-specific method for quantitating the DNA in a sample which does not require the use of radioactivity.

The quality of a DNA sample is conventionally evaluated by agarose gel size fractionation of the DNA followed by ethidium bromide staining. High quality, i.e. undegraded, genomic DNA consists primarily of high molecular weight DNA. Degradation of the DNA produces fragments of random lengths which yield a smear of lower molecular weight DNA on the gel. Because ethidium bromide does not readily stain denatured (single-stranded) DNA, conventional methods are unsatisfactory for samples that are extracted using methods that require heating or boiling steps or alkaline treatment. For example, the Chelex method of DNA extraction for amplification using the polymerase chain reaction requires boiling for cell lysis (Walsh et al., 1991, *BioTechniques* 10(4):506–513, incorporated herein by reference). Some DNA extraction methods require heating to 95° C for inactivation of proteinase K (see Higuchi, 1979, in Erlich (ed.) *PCR Technology: Principles and Applications for DNA Amplification*, (Stockton Press, New York):31–38, incorporated herein by reference. There is a need for a sensitive method of assessing the quality of both single- and double-stranded DNA samples. The present invention meets these needs.

SUMMARY OF THE INVENTION

The present invention provides sensitive methods for the quantitation of human nuclear and mitochondrial DNA contained in a sample that are both simple and rapid to carry out. The DNA is immobilized on a membrane, hybridized with a biotinylated probe that hybridizes to a repeated human genomic sequence or to a mitochondrial sequence and detected using a chemiluminescent assay. In one embodiment, the repeated human sequence is the human alpha satellite locus, D17Z1. In another embodiment, the sequence is part of the control region of the mitochondrial genome. The quantity of DNA contained in the sample is estimated from the amount of hybridized probe detected. The entire procedure can be completed in 1.5 hours and can detect less than 75 pg of human DNA.

In addition, the present invention provides methods of evaluating the quality of DNA contained in a sample. The DNA is size fractionated by gel electrophoresis, immobilized on a membrane, hybridized with a biotinylated probe that hybridizes to a repeated human genomic sequence, and detected using a chemiluminescent assay. In one embodiment, the repeated human sequence is the human alpha satellite locus, D17Z1. The quality of the DNA is estimated from the fragment size pattern observed.

The present invention also provides biotinylated oligonucleotide probes that hybridize to sequences within the human alpha satellite locus, D17Z1, and to sequences within the mitochondrial control region for use in the methods provided.

The present invention also provides kits containing reagents used in the methods of the present invention.

BRIEF DESCRIPTION OF THE DRAWINGS

FIG. 2A illustrates a photograph of a 1% agarose gel. Human genomic DNA (14 nanograms) was boiled in either 5% Chelex or water for 0, 1, 3, or 8 minutes and then subjected to electrophoresis. DNA size markers were run concurrently on the gel and are indicated by "M". The DNA was subsequently transferred to a nylon membrane, hybridized with the probe, SW49 (SEQ ID No. 1), and visualized by chemiluminescent detection with a 15 minute exposure to film. FIG. 2B illustrates the resulting photograph. Photograph labels are as in FIG. 2A.

DETAILED DESCRIPTION OF THE PREFERRED EMBODIMENTS

Figure 1:
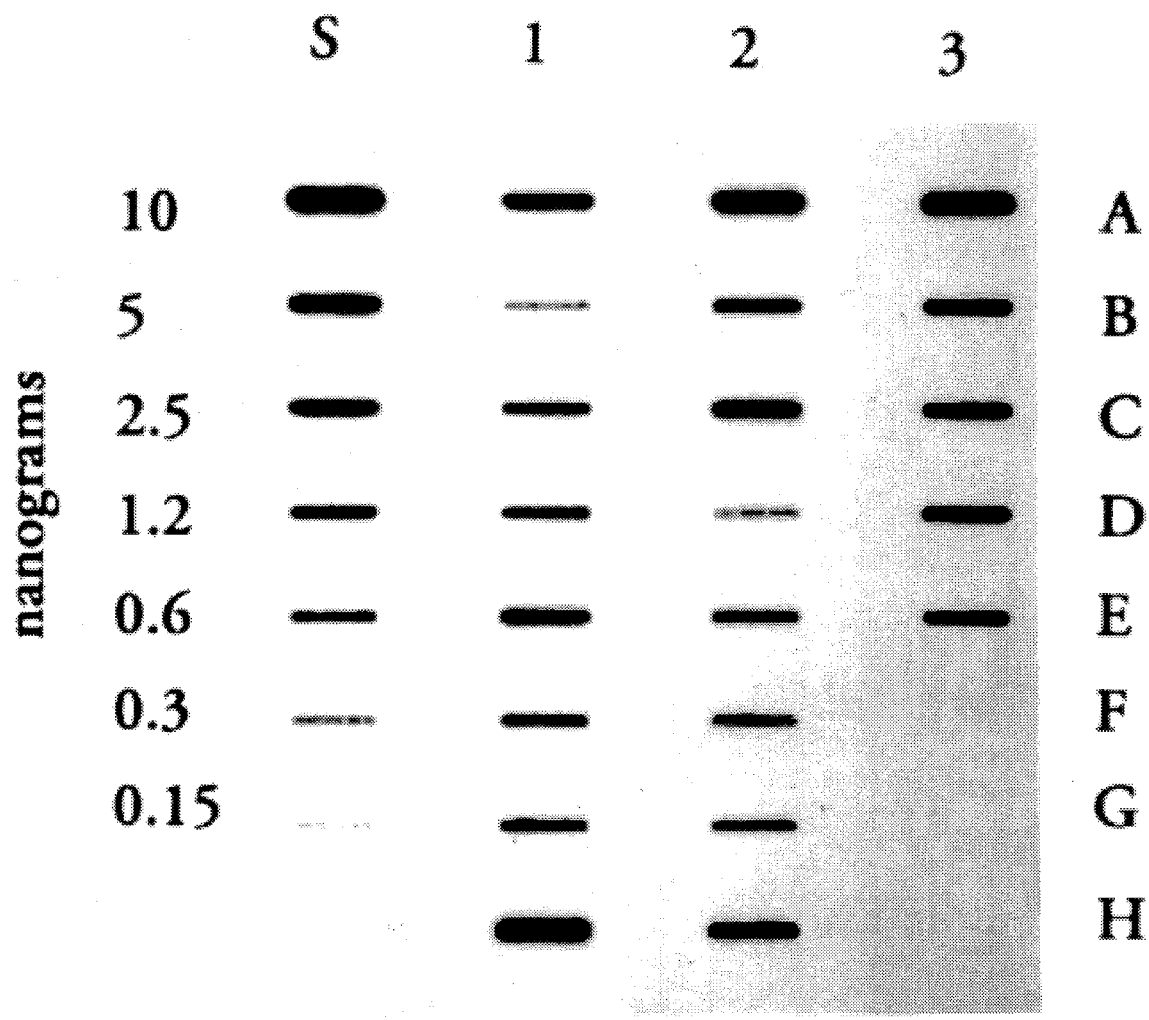
FIG. 1 illustrates the results of a DNA quantity assay as described in Example 2. Sample DNA was immobilized on a nylon membrane and hybridized with the probe, SW49 (SEQ ID No. 1). Bands were visualized using chemiluminescent detection with a 15 minute exposure to film. Colturin "S" is a human genomic DNA titration series ranging from 10 to 0.15 nanograms of DNA. Columns 1–3 are samples in which the DNA quantity was unknown. The sources of the extracted DNA samples in columns 1–3 were as follows: 1A–1E were bloodstains, 1F–2C were whole blood, 2D–3B were single hairs, 3C–3E were buccal samples, 3F was 1 µg of cow DNA, 3G was 1 µg mouse DNA; no sample was added to 3H.

The term "sample" as used herein refers to any substance containing or presumed to contain nucleic acid including, but not limited to, tissue or fluid isolated from one or more individuals, in vitro cell culture constituents, as well as evidential, clinical, archival, and ancient samples.

The terms "oligonucleotide" and "nucleic acid" as used herein refer to molecules comprising two or more deoxyribonucleotides or ribonucleotides. The exact size will depend upon many factors, which in turn depend on the ultimate function or use of the oligonucleotide. The terms refer to both single- and double-stranded DNA and RNA. Oligonucleotides may be derived by any suitable technique including, but not limited to, isolation of an existing or natural sequence, chemical synthesis, DNA replication or amplification, reverse transcription, or a combination thereof. Chemical synthesis methods may include, for example, the phosphotriester method described by Narang et al., 1979, *Methods in Enzymology* 68:90, incorporated herein by reference, the phophodiester method described by Brown et al., 1979, *Methods in Enzymology* 68:109, incorporated herein by reference, the diethylphosphoramidite method described by Beaucage et all., 1981, *Tetrahedron Letters* 22:1859, incorporated herein by reference, and the solid support method disclosed in U.S. Pat. No. 4,458,066, incorporated herein by reference. Oligonucleotide synthesis is described in Levenson and Chang, 1990, in *PCR Protocols,* Innis et al. (eds.), Academic Press, New York:99–112, incorporated herein by reference.

The term "subsequence" as used herein refers to a nucleotide sequence which is wholly contained within another nucleotide sequence. As defined, a sequence is also a subsequence of itself. As used herein, a subsequence suitable as a hybridization probe is about 10–140 nucleotides in length and preferably 40–130 nucleotides in length.

The term "quality" as used herein refers to the degree of degradation of a DNA sample. A high quality sample contains DNA which has undergone little or no degradation. The quality of a DNA sample can be assessed by measuring the molecular weight of the sample DNA by gel electrophoretic size fractionation. For example, using a 1% agarose gel, a high quality sample of human genomic DNA migrates with a 20 kb DNA marker and forms a relatively tight band when visualized either by ethidium bromide staining or by the methods of the present invention, whereas in a low quality human DNA sample, degradation of the DNA yields fragments of varying length which appear as a smear of lower molecular weight DNA, i.e., less than 20 kb.

The terms "probe" and "oligonucleotide probe" as used herein refer to labeled oligonucleotides which are sufficiently complementary to a specific target sequence contained in a DNA sample to form a stable hybridization duplex with the target sequence. The hybridization is under stringent conditions. Stringent hybridization conditions are well known in the art and are described, for example, in Sambrook et al., 1989, *Molecular Cloning: A Laboratory Manual,* Second Edition, Cold Spring Harbor Laboratory, New York, incorporated herein by reference. The term "hybridizing region" refers to that region of an oligonucleotide probe which is complementary to, and therefore hybridizes to, the target sequence. Although the hybridizing region typically refers to the entire oligonucleotide, the probe may include additional nucleotide sequences which function, for example, as the label binding site to provide means for fixing the probe sequence to a solid support. In the preferred mode, the hybridizing region of the oligonucleotide probe is completely complementary to the target sequence. However, in general, complete complementarity is not necessary; stable duplexes may contain mismatched bases or unmatched bases. Modification of the stringent conditions may be necessary to permit a stable hybridization duplex with one or more base pair mismatches or unmatched bases. Sambrook et al., 1989, supra, provides guidance for suitable modification. Stability of the target/probe duplex depends on a number of variables including length of the oligonucleotide, base composition and sequence of the oligonucleotide, temperature, and ionic conditions.

The oligonucleotide probes of the present invention are labeled to permit detection of probe-target hybridization duplexes. In general, a label can be any atom or molecule which can be attached to the oligonucleotide probe and used to provide a detectable, quantifyable signal. Labels may be attached to an oligonucleotide directly or indirectly by a variety of techniques. Depending on the type of label used, the label can be attached to a terminal (5' or 3' end of the probe) or a non-terminal nucleotide, and can be attached indirectly through spacer arms of various sizes and compositions. Using commercially available phosphoramidite reagents, one can produce oligomers containing functional groups (e.g., thiols or primary amines) at either the 5' or 3' terminus via an appropriately protected phosphoramidite, and can label such oligonucleotides using protocols described in, for example, *PCR Protocols: A Guide to Methods and Applications* (Innis et al, eds. Academic Press, Inc., 1990). In a preferred embodiment, the label consists of a biotin molecule covalently bound to the oligonucleotide at the 5' end. The term "biotinylated probe" as used herein refers to a probe with one or more biotin molecules bound either directly to the oligonucleotide or indirectly through intervening "spacer" molecules.

Detection of the probe is preferably by a chemiluminescent assay using a luminol-based reagent as described in Whitehead, et al., 1983, *Nature* 30.5:158–159, incorporated herein by reference, and available commercially (ECL, Amersham, Arlington Heights, Ill.). Following hybridization of the probe with the target DNA, the biotin molecule attached to the probe oligonucleotide is conjugated to streptavidin-horseradish peroxidase (SA-HRP). Alternatively, the oligonucleotide probe can be labeled with horseradish peroxidase directly, thereby eliminating the separate conjugation step. In either case, subsequent oxidation of luminol by the horseradish peroxidase enzyme results in the emission of photons, which is then detected on standard autoradiography film. The intensity of the signal on the film is a function of DNA quantity. A series of DNA standards containing known amounts of DNA are assayed along with one or more unknown samples, blotted on the same membrane. The signal intensities of the known DNA standards allows an empirical determination of the functional relationship between signal intensity and DNA quantity, which enables the quantitation of the unknown samples.

Alternatively, probe/target hybridization duplexes may be detected using a color development reaction as described in Sheldon et al., 1986, *Proc. Natl. Acad. Sci. USA* 83:9085–9089, incorporated herein by reference, which utilizes 3,3',5,5'-tetramethylbenzidine (TMB) and hydrogen peroxide.

The probes of the invention are complementary to a highly-repetitive human genomic sequence. High sensitivity is obtained from the use of a repetitive sequence because the high copy number per genome of a repeat sequence provides a large number of target sequences for hybridization. Numerous repetitive sequences are known to occur in the human genome, such as satellite DNA and the Alu repeat sequences (Brilten et al., 1988, *Proc. Natl. Acad. Sci. USA* 85:4770–4774). Alpha satellite DNA is a complex family of tandemly repeated DNA located primarily at the centromeres of primate chromosomes (Waye and Willard, 1986, *Molecular and Cellular Biology* 6(9):3156–3165, Willard, 1985, *American Journal of Human Genetics* 37:524– 532, both incorporated herein by reference). In a preferred mode, the probes are complementary to D 17Z1, a primate specific alpha satellite DNA sequence located on chromosome 17. The sequence is estimated to be present in 500 to 1,000 copies per chromosome 17 (Waye and Willard, 1986, supra). The primary D 17Z1 repeat sequence is 2.7 kb in length and is arranged as 16 contiguous monomers; a less abundant (approximately 100 copies per chromosome 17) repeat consisting of 15 tandem monomers is also found.

In another embodiment of the invention, the probes are complementary to sequences specific to the mitochondrial genome. The mitochondrial control region has been extensively characterized at the sequence level, and it contains two hypervariable regions surrounded by relatively conserved regions (Vigilant et al., 1989, *Proc. Natl. Acad. Sci. USA* 86:9350–9354, incorporated herein by reference). Two pairs of primers complementary to the conserved regions have been used to amplify the hypervariable regions using the PCR. These regions can be analyzed subsequently by direct DNA sequencing or by hybridization to a collection of sequence-specific oligonucleotide probes (Vigilant et al., Supra., and Stoneking et al., 1991, *Am J. Hum. Genet.* 48:370–382, incorporated herein by reference). In a preferred mode, the quantitation probes contain sequences overlapping the control region primer sites or sequences within the conserved areas of the control region.

In a preferred DNA quantitation method, a DNA sample is immobilized on a nylon membrane before hybridizing with the labeled probes as described in Example 2. A commercially available apparatus (e.g., the Convertible, GIBCO BRL, Gaithersburg, Md.) may be used to immobilize the DNA sample on the membrane in a specified location. Thus, a large number of samples can be immobilized on the same membrane in a defined array. Simultaneous hybridization of numerous samples can be effected by immersion of the membrane in a hybridization buffer containing the quantitation probe. The methods of the present invention are particularly suited to applications in which a large number of samples need to be analyzed on a routine basis, such as in a commercial environment.

In a preferred DNA quality assay method, after size fractionation of the DNA sample by agarose gel electrophoresis, the fractionated DNA is transferred to a nylon membrane before hybridizing with the probes of the present invention. The DNA may be transferred using a commercially available apparatus (e.g., the Posiblot transfer system, Stratagene, La Jolla, Calif.). After the DNA is transferred to the nylon membrane, the DNA may be fixed to the membrane by baking at 80° C., as described in Example 3, or by crosslinking of the thymidine residues to the membrane by UV irradiation (Church and Gilbert, 1984, *Proc. Natl. Acad. Sci. USA* 81:1991–1995, incorporated herein by reference).

Reagents employed in the methods of the present invention can be packaged into kits. Kits include the labeled oligonucleotide probe or, if unlabeled, specific labeling reagents may be included. The kits may also include suitably packaged reagents and materials needed for DNA immobilization and detection, such membranes, buffers, enzymes, DNA standards, and a hybridization tray, as well as instructions for conducting the assay.

The following examples are offered by way of illustration and are not intended to limit the invention in any manner.

EXAMPLE 1

Probes

The probes of the present invention are complementary to a region contained within the 2.7 kb D17Z1 locus. Each oligonucleotide is bound to a biotin molecule at the 5' end either directly or through a phosphoramidite "spacer" molecule. Probes SW49 (SEQ ID No. 1), SW1000 (SEQ ID No. 1), SW1001 (SEQ ID No. 1), SW1002 (SEQ ID No. 1), SW1003 (SEQ ID No. 1), SW1004 (SEQ ID No. I), and SW1005 (SEQ ID No. 1) were constructed with the identical oligonucleotide sequence, differing in the derails of the label. The nucleotide sequence common to each of the probes is provided below and in the Sequence Listing.

| SEQ ID No. | Sequence |
| --- | --- |
| 1 | 5TAGAAGCATTCTCAGAAACTACTTTGTGATGATTGCATTC |

Oligonucleotide synthesis was performed on an automated DNA synthesizer (either Milligea/Biosearch 8750, Applied Biosystems 394; or Eppendorf Biotronik D) on a micromole scale using 500 angstrom controlled-pore glass supports and O-cyanoethyl N,N-diisopropyl phosphoramidites as described in Beaucage and Caruthers, 1981, *Tetrahedron Letters,* 22:1859–1862 and Sinha et al., 1984, *Nucleic Acids Research,* 12:4539–4557, both incorporated herein by reference. Supports and phosphoramidite derivatives of dA, dC, dG, and T were obtained commercially from Millipore/Waters, Bedford, Mass.; or Cruachem, Sterling, Va. Biotin and "Spacer" phosphoramidites were obtained from Glen Research, Sterling, Va. Two biotin reagents were used: Biotin Phosphoramidite and BioTEG Phosphoramidite. These two biotin reagents differ in that the BioTEG product includes a longer spacer separating the biotin from the oligonucleotide. Oligonucleotides were synthesized with the terminal dimethoxytrityl group left intact and were purified by lipophilic selection using solid-phase extraction cartridges (PREP-NENSORB, du Pont). Biotinylation and oligonucleotide purification are described in Misiura et al., 1990, *Nucleic Acids Research* 18:4345–4354; Alves et al., 1989, *Tetrahedron Letters,* 30:3089–3092; and Pon, 1991, *Tetrahedron Letters* 32:17 15–17 18, all of which are incorporated herein by reference.

Quantitation probes SW49 (SEQ ID No. 1), SW1000 (SEQ ID No. 1), SW1001 (SEQ ID No. 1), SW1002 (SEQ D No. 1), SW1003 (SEQ ID No. 1), SW1004 (SEQ ID No. 1), and SW1005 (SEQ ID No. 1) are shown schematically in Table 1, below. In Table 1, B I refers to Biotin Phosphoramidite, B2 refers to BioTEG Phosphoramidite, Spacer refers to a phosphoramidite spacer. Oligo refers to the oligonucleotide (SEQ ID No. 1) common to the probes. mtOligo refers to mitochondrial DNA oligonucleotides (sequences provided below). Probes SW 1000 (SEQ ID No. 1) and SW1003 (SEQ ID No. 1) are identical in sequence and label to SW49 (SEQ ID No. 1).

TABLE 1

| SEQ ID No. | Probe | Construct |
|---|---|---|
| 1 | SW49 | B1-Oligo |
| 1 | SW1000 | B1-Oligo |
| 1 | SW1001 | B1-Spacer-Oligo |
| 1 | SW1002 | B1-Spacer-B1-Spacer-Oligo |
| 1 | SW1003 | B1-Oligo |
| 1 | SW1004 | B2-Oligo |

TABLE 1-continued

| SEQ ID No. | Probe | Construct |
|---|---|---|
| 1 | SW1005 | B2-Spacer-Oligo |
| 12–20 | RR64–RR72 | B2-mtOligo |

Additional oligonucleotide probe sequences useful in the methods of the present invention are provided below.

| Probe | SEQ ID No. | Sequence |
|---|---|---|
| SW31 | 2 | 5'CACTATTTGTAGAATGTGCAAGTGGATATTTAGGCCTCTC |
| SW32 | 3 | 5'CAGAAGCATTCTCAGAACCTTCTTCGTGATGTTTGCATTC |
| SW33 | 4 | 5'TAGAAGCATTCTCAGAAACTACTTTGTGATGATTGCATTCAAGTC ACAGAGTTGAACATTCCCTTTGACAGAGCAGTTTGGAAACTCTCTCTT TGTGTAGAATCTGCAAGTGGAGATATGGACCGCTTTAGG |
| SW34 | 5 | 5'CAGTAGCATTCACAGAAAACTCTTGGTGACGACTGAGTTTAACT CACAGAGCTGAACATTCCTTTGGATGGAGCAGTTTCGAAACACAC TATTTGTAGAATGTGCAAGTGGATATTTAGGCCTCTCTGAGG |
| SW35 | 6 | 5'CAGAAGCATTCTCAGAACCTTCTTCGTGATGTTTGCATTCAACTC ACAGTGTTGAACCTTCTTTGATAGTTCAGGTTTGAAACGGTCTTTC TGTAGAAACTGCAAGTAGATATTTGGACCGCTCTGAGG |
| SW56 | 7 | 5'GAAACTCTCTTGTGTAGAATCTGCAAGTGGAGATATGGA |
| SW59 | 8 | 5'AAGTCACAGAGTTGAACATTCCCTTTGACAGAGCAGTTTG |
| SW52 | 9 | 5'TAGAAGCATTCTCAGAAACTACTTGTGATGATTGCATTCAGTC ACAGAGTTGAACATT |
| SW57 | 10 | 5'TAGAAGCATTCTCAGAAACTACTTTGTGATGATTGCATTCAAGTC ACAGAGTTGAACATTCCCTTTGACAGAGCAGTTTG |
| SW58 | 11 | 5'TAGAAGCATTCTCAGAAACTACTTTGTGATGATTGCATTCAAGTC ACAGAGTTGAACATTCCCTTTGACAGAGCAGTTTGGAAACTCTCTT TGTGTAGAA |

The oligonucleotide probe sequences are subsequences of the D17Z1 constituent monomers. SW33 (SEQ ID No. 4) is a subsequence of monomer 11, SW34 (SEQ ID No. 5) is a subsequence of monomer 12, and SW35 (SEQ ID No. 6) is a subsequence of monomer 13. The other oligonucleotide sequences are subsequences of one of the above 3 oligonucleotides. SEQ ID No. 1, SW56 (SEQ ID No. 7), and SW59 (SEQ ID No. 8) are non-overlapping subsequences of SW33 (SEQ ID No. 4). SEQ ID No. 1 is a subsequence of SW52 (SEQ ID No. 9), which is a subsequence of SW57 (SEQ ID No. 10), which is a subsequence of SW58 (SEQ ID No. 11), which are all subsequences of SW33 (SEQ ID No. 4). SW31 (SEQ ID No. 2) is a subsequence of SW34 (SEQ ID No. 5), and SW32 (SEQ ID No. 3) is a subsequence of SW35 (SEQ ID No. 6).

Additional probes of the present invention are complementary to various conserved sequences within the mitochondrial control region.

| Probe | SEQ ID No. | Sequence |
|---|---|---|
| RR64 | 12 | 5'GGCGGTATGCACTTTTAACAGTCACCCCCCAACTAACAC |
| RR65 | 13 | 5'GTCTTTAACTCCACCATTAGCACCCAAAGCTAAGATTCTA |
| RR66 | 14 | 5'CGTGAAATCAATATCCCGCACAAGAGTGCTACTCTCCTCG |
| RR67 | 15 | 5'GAACTGTATCCGACATCTGGTTCCTACTTCAGGGTCATAAAGC |
| RR68 | 16 | 5'GACATCACGATGGATCACAGGTCTATCACCCTATTAACCAC |
| RR69 | 17 | 5'CATCCTCCGTGAAATCAATATCCCGCACAAGAGTGCTAC |
| RR70 | 18 | 5'GTCTTTAACTCCACCATTAGCACCCAAAGC |
| RR71 | 19 | 5'CTCCACCATTAGCACCCAAAGCTAAGATTC |
| RR72 | 20 | 5'GTATCCGACATCTGGTTCCTACTTCAGGGTC |

RR70 (SEQ ID No. 18) and RR721 (SEQ ID No. 19) are overlapping subsequences of RR65 (SEQ ID No. 13). RR72 (SEQ ID No. 20) is a subsequence of RR67 (SEQ ID No. 15). RR66 (SEQ ID No. 14) and RR69 (SEQ ID No. 17) overlap.

EXAMPLE 2

DNA Quantity Estimation

To estimate the quantity of DNA in a sample, extracted sample DNA was immobilized on a nylon membrane along with a titration series of a human genomic DNA standard and hybridized to the biotinylated probe, SW49 (SEQ ID No. 1). The synthesis of the probe was as described in Example 1, above. Hybridization was visualized using a chemiluminescence detection protocol. The quantity of DNA present in the sample was estimated by comparison of the hybridization signal obtained from the sample DNA to those obtained from the DNA standards. Details of the experimental protocol are as follows.

The quantities of human DNA in extracts from 5 human bloodstain samples, 6 human whole blood samples, 7 human hair samples, and 3 human buccal samples were estimated. In addition, samples consisting of 1 µg cow DNA and 1 µg mouse DNA were also used as a rest of probe specificity. DNA was extracted from samples either by the Chelex method described in Walsh et al., 1991, supra., or by a salting out method as described in Miller et al., 1988, *Nucl. Acids Res.* 6(3): 1215, incorporated herein by reference. In the Chelex method, a 3 mm$^2$ bloodstain, a buccal scraping, or a 1 cm hair root section were incubated in 200 µl 5% Chelex at 56° C., followed by boiling for 8 minutes.

Five µl of each extracted DNA sample was added to 100 µl spotting buffer (0.4 N NaOH, 25 mM EDTA). DNA standards were prepared by adding the following quantities of human DNA to 100 µl spotting buffer: 10, 5, 2.5, 1.2, 0.6, 0.3, 0.15 ng. A blank was also prepared which contained no DNA added to 100 µl spotting buffer. A piece of Biodyne B Membrane (Part Biosupport, Glen Cove, N.Y.) was pre-wet in distilled water and placed in a slot blot apparatus (The Convertible, 0.75×0.75 mm, GIBCO BRL, Gaithersburg, Md.). The sample and standard preparations were added to the wells (entire volume) then the vacuum was applied. With the membrane still in the apparatus, 200 µl of 15% hydrogen peroxide was added to each well, and the vacuum was applied again.

The membrane was removed from the apparatus and immediately placed in 200 ml of prehybridization solution consisting of 5×SSPE (20×SSPE is 3.6M NaCl, 200 mM NaH$_2$PO$_4$—H$_2$O, 20 mM EDTA, pH 7.4) and 0.5% sodium dodecyl sulfate (SDS) prewarmed to 50° C. and incubated in a shaking water bath for 15 minutes at 50° C. The membrane was transferred to 30 ml hybridization buffer (5×SSPE, 0.5% SDS) containing 15 pmoles of the probe, SW49 (SEQ [D No. 1), incubated in a shaking water bath for 15 minutes at 50° C. to allow hybridization to occur, and then rinsed briefly in 1.5×SSPE, 0.5% SDS. The stringent wash and conjugation (biotin to SA-HRP) steps were carried out simultaneously. The membrane was placed in 30 ml of 1.5×SSPE, 0.5% SDS containing 90 µl of SA-HRP (Perkin Ehner, Norwalk, Conn.) and incubated in a shaking water bath for 10 minutes at 50° C. The membrane was rinsed briefly in 1.5×SSPE, 0.5% SDS and then washed in 200 ml of 1.5×SSPE, 0.5% SDS on an orbital shaker for 15 minutes at room temperature. The membrane was then rinsed in 0.1M Sodium Citrate, pH 5.

Detection of the hybridized probe was carried out using ECL (Amersham, Arlington Heights, Ill.), which is a luminol-based reagent used for enhanced chemiluminescent detection. The membrane was placed in a mixture of 10 ml of ECL Reagent 1 and 10 ml of ECL Reagent 2 and shaken for 1 minute at room temperature. The membrane was placed on a sheet of Benchkote (Whaunan, Maidstone, England), covered with Saran Wrap, and wiped free of excess moisture. To visualize the DNA, the membrane was exposed to Hyperfilm (Amersham, Arlington Heights, Ill.) or Kodak XAR5 film (Kodak, Rochester, N.Y.) for 15 minutes at room temperature. Results are shown in FIG. 1.

DNA quantitation was determined both by visual comparison of sample DNA slot blot intensities to those of the DNA standards and by computer image analysis of the slot blot results on film. For the computer analysis of the slot blot results, the film was scanned using an 8-bit gray-scale flatbed scanner (available from Abaton Corporation, Fremont, Calif.) and the resulting picture analyzed using the computer program Image 1.41 (written by Wayne Rasband and available from NIH, Bethesda, Md.) running on a Macintosh computer. The mean signal density (actually scanned pixel values ranging from 0 to 255) of each slot blot signal was measured. The mean signal density was defined over a rectangle of constant size that wholly contained the slot blot signal. A comparison of mean signal densities defined and measured in this manner is equivalent to a comparison of the total signal from each slot blot. The background density, measured next to each slot, was subtracted from each mean density. Background signal was not observed on the membrane directly, and was most likely an artifact of the scanning of the film. This data was then exported to another computer program (Kaleidagraph, Abelback Software) fit into an equation describing the relationship between slot blot mean signal density and the DNA quantity to the data from the DNA standards. The data closely fit the exponential equation $Y = C \cdot e^{(r \cdot x)}$ where Y is the DNA quantity, in nanograms, C=0.1787 nanograms, r=0.0308, and X is the mean signal density. Signal density, defined here as scanned pixel values, is a dimensionless number between 0 and 255. Once determined, this exponential equation was used to determine the quantity of DNA in the unknown samples from the mean signal density measurements.

The quantity of DNA in the each of the samples containing human DNA was estimated from the observed slot blot results using the above equation. The DNA quantity estimates are shown below. Sample positions refer to the column and row positions indicated in FIG. 2. No signal was observed from cow or mouse DNA samples, indicating that the probe SW49 (SEQ [D No. 1) hybridized specifically to human DNA only.

| Sample | Source | Quantity (ng) |
|---|---|---|
| 1A | Bloodstain | 2.24 |
| 1B | " | 0.26 |
| 1C | " | 1.07 |
| 1D | " | 0.88 |
| 1E | " | 1.74 |
| 1F | Whole Blood | 0.83 |
| 1G | " | 1.09 |
| 1H | " | 7.17 |
| 2A | " | 6.32 |
| 2B | " | 1.32 |
| 2C | " | 2.33 |
| 2D | Hair | 0.28 |
| 2E | " | 0.94 |
| 2F | " | 0.52 |
| 2G | " | 0.68 |
| 2H | " | 2.49 |
| 3A | " | "6.34 |
| 3B | " | 1.64 |
| 3C | Buccal | 1.46 |
| 3D | " | 1.49 |
| 3E | " | 1.00 |
| 3F | Cow DNA | 0 |
| 3G | Mouse DNA | 0 |

To estimate the quantity of mitochondrial DNA in a sample, the protocol described above for quantitation of nuclear DNA is used with the following exceptions:

1. Prehybridization is performed at 46° C. instead of 50° C.
2. Hybridization is performed at 46° C. with 20 pmoles of the probe RR70 (SEQ ID No. 18).

A commercially available preparation of placental DNA (SIGMA) is diluted and used for the DNA standards. Since the extracted placental DNA contains a mixture of nuclear and mitochondrial DNA, the standards can be used for both types of quantity estimates. Mitochondrial DNA is the minor component of the total DNA preparation and is present in an unknown quantity. Therefore, to use placental DNA (or other total DNA) preparations as a standard for the mitochondrial DNA quantitation assay, the amount of mitochondrial DNA present must be determined. This value can be obtained using a purified mitochondrial DNA preparation that has been quantitated spectrophotometrically. Dilutions of the purified DNA can then be hybridized with the mitochondrial DNA-specific probe as described above at the same time as the total DNA dilutions, and the signal intensities can be compared to determine the quantity of mitochondrial DNA in the total DNA preparation. Obviously, a purified mitochondrial DNA sample would be the ideal quantitation standard, but the procedure for isolating mitochondrial DNA is extremely time consuming, expensive, and provides a very low-yield.

EXAMPLE 3

DNA Quality Estimation

Purified human genomic DNA was diluted to 2 ng/µl in both 5% Chelex and glass distilled water, and then boiled for 0, 1, 3, or 8 minutes in a boiling water bath. Seven µl (14 ng) of each sample was subjected to electrophoresis on a 1% agarose gel containing 0.5 µg/ml ethidium bromide in 1×TBE for 30 minutes at 100 volts. The gel was photographed, soaked in 0.25M HCl for 15 minutes to depurinate the DNA, and then soaked in 0.5 N NaOH, 1.5M NaCl for 10 minutes to denature the DNA. The DNA was transferred to a Biodyne B membrane using the Posiblot transfer system (Stratagene, La Jolla, Calif.). Transfer was performed at 75 mm Hg for 1 hour using 10× SSPE as the transfer buffer. The membrane was baked in a vacuum oven for 15 minutes at 80° C. to fix the DNA. The membrane was wetted with 2×SSPE and then soaked in 15% hydrogen peroxide for 2 minutes. Hybridization and detection of bound SW49 probe (SEQ ID No. 1) was performed essentially as described in Example 1, above, except that the blot was exposed to film for 30 minutes.

Figure 2A:
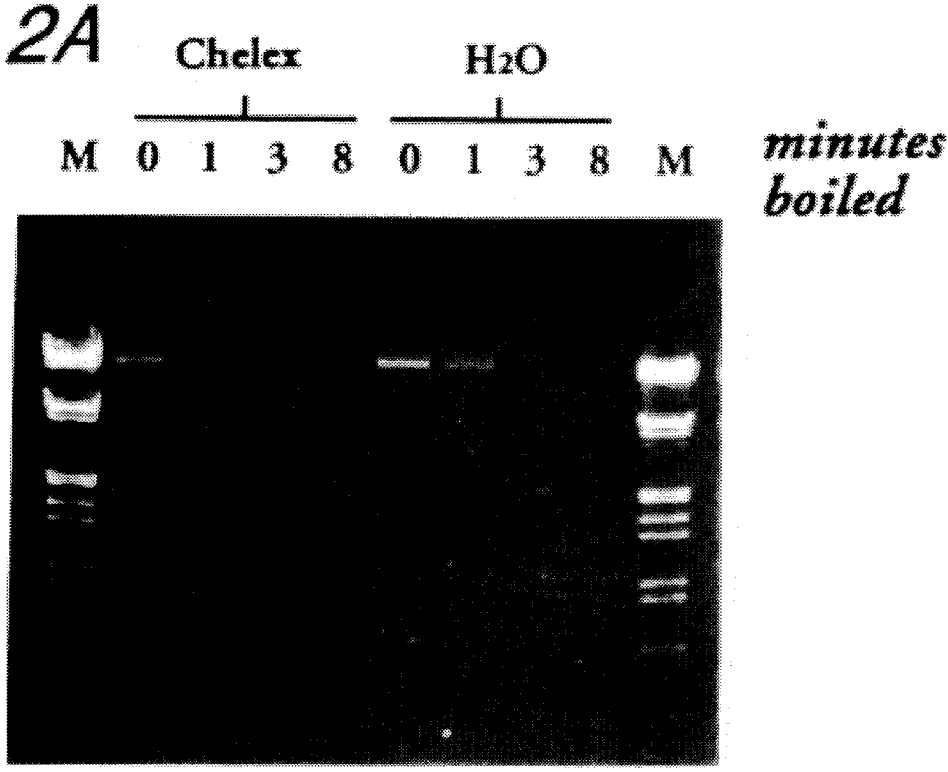
FIGS. 2A and 2B illustrate the results of a DNA quality assay as described in Example 3.
Figure 2B:
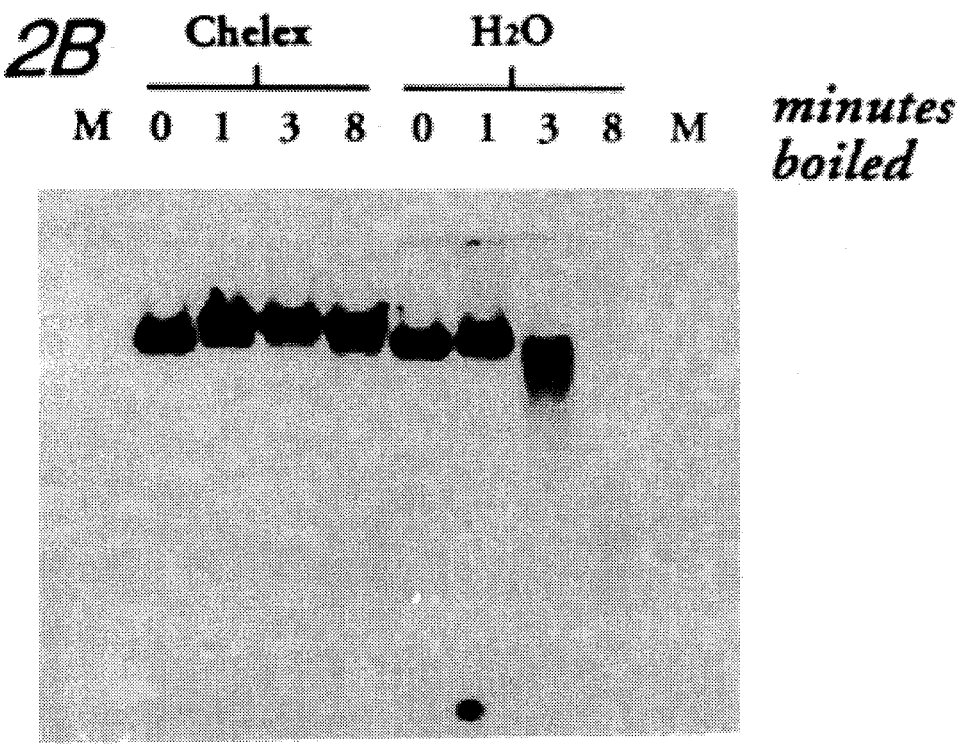

The results, shown in FIGS. 2A and 2B, indicate that the methods of the present invention for the evaluation of DNA quality provide improved detection sensitivity, particularly for the analysis of denatured DNA. In this analysis (1% agarose gel), undegraded genomic DNA runs as a relatively tight band at about 20 kb relative to an appropriate molecular marker; degraded DNA appears as a smear of DNA below 20 kb in molecular weight. The photograph of the ethidium bromide-stained agarose gel, shown in FIG. 2A, shows weak or absent band intensities for the boiled samples using ethidium bromide detection, particularly for the samples boiled in water. This is because ethidium bromide does not readily stain denatured (single-stranded) DNA. As shown in FIG. 2B, DNA boiled in Chelex remains relatively intact. The double band for the sample boiled in Chelex for 1 minute presumably corresponds to both denatured and non-denatured DNA. After 3 to 8 minutes of boiling in Chelex, all DNA is denatured. The presence of a single band of high molecular weight indicates that little degradation occurred from boiling in Chelex. In contrast, DNA boiled in water shows slight degradation after 3 minutes and significant degradation after 8 minutes, as indicated by the smear of lower molecular weight DNA apparent. The increased detection sensitivity realized by blotting and probing using the methods of the present invention allow for a greatly improved ability to evaluate the effects of boiling on DNA quality.

EXAMPLE 4

Probe Labeling

A comparison of the effect of different probe label moieties on the sensitivity of the DNA quantity assay was done using probes SW49 (SEQ ID No. 1), SW1000, SW1001 (SEQ ID No. 1), SW1002 (SEQ ID No. 1), SW1003 (SEQ ID No. 1), SW1004 (SEQ ID No. 1), and SW1005 (SEQ ID No. 1). As described in Example 1, above, the oligonucleotide sequence of each of these probes is identical SW49 (SEQ ID No. 1); these probes differ in the number and spacing of the biotin labels bound to the oligonucleotide. For comparison, subsets of the probes listed above were used in the quantity assay essentially as described in Example 2, above.

One comparison was done using probes SW1000 (SEQ ID No. 1), SW1001 (SEQ ID No. 1), and SW1002 (SEQ ID No. 1). Probe SW1001 (SEQ ID No. 1) showed a slight increase in sensitivity compared to probe SW1000 (SEQ ID No. 1). Because these probes differ only in the presence of a spacer in SW 100 1 (SEQ ID No. 1), the improvement in assay sensitivity most likely resulted from an increase in the space between the oligonucleotide and the biotin label. Probe SW1002 (SEQ ID No. 1), which contains two biotin molecules per probe, showed increased sensitivity (increased signal for 150 picograms with a 15 minute exposure) over both of the single-biotin probes.

Another comparison was done using probes SW1001 (SEQ ID No. 1), SW1004 (SEQ ID No. 1), and SW1005 (SEQ ID No. 1). From the comparison of SW1001 (SEQ ID No. 1) and SW1004 (SEQ ID No. 1), it was observed that biotinylation using BioTEG phosphoramidite (SW1004—SEQ ID No. 1), which, in effect, contains a spacer, is equivalent to, or even superior to, biotinylation using biotin phosphoramidite and a separate phosphoramidite spacer (SW 100 1—SEQ ID No. 1). Probe SW1005 (SEQ ID No. 1), which incorporates both BioTEG phosphoramidite and a separate phosphoramidite spacer, provided the greatest sensitivity.

EXAMPLE 5

Assay Sensitivity

In each of the DNA quantity assays described in Examples 2 and 4, above, visualization of the slot blot results was accomplished using a 15 minute film exposure. With a 15 minute exposure time, assay sensitivity in the range of 75 picograms was seen for nuclear DNA quantitation. Increasing the exposure time can increase the sensitivity of the assay. This was demonstrated by a DNA quantity assay essentially as described in Example 2 using probe SW 1004 (SEQ ID No. 1) and with both 15 minute and 3 hour exposures. Whereas sensitivity down to 75 picograms could be detected with a 15 minute exposure, the 3 hour exposure showed sensitivity down to between 9 and 18 picograms.

EXAMPLE 6

Preferred Method for Determining the Quantity of DNA in a Sample

Slot Blot Protocol
1. Add 1 to 5 µl of each DNA sample to 150 µl of spotting buffer (0.4 N NaOH, 25 mM EDTA, 0.0015 % Bromophenol Blue). Also add the following quantities of DNA standard (in 5 µl) to 150 µl of spotting buffer: 10, 5, 2.5, 1.2, 0.6, 0.3, 0.15 ng.
2. Pre-wet Biodyne B membrane in 50 mL of 0.4 N NaOH, 25 mM EDTA (5–30 minutes).
3. Place the membrane in the slot blotter, and pipette the entire volume for each sample into the wells. Apply spotting buffer containing no DNA to some of the empty wells as a negative control. Turn on the vacuum only after all samples have been applied.
4. Begin the pre-hybridization step immediately (see below).

Hybridization and Detection
1. Pre-Hybridization: Place the membrane in 150 mL of pre-warmed 5×SSPE, 0.5% SDS. Then add 5 mL of 30% $H_2O_2$. Shake in a water bath (70 rpm) for 15 minutes at 50° C.
2. Hybridization: Incubate in 30 mL of 5×SSPE, 0.5% SDS containing 20 pmoles SW1004, for 20 minutes at 5(PC in a shaking water bath (70 rpm). Rinse: Briefly rinse in 1.5×SSPE, 0.5% SDS.
3. Stringent Wash/Conjugation: Incubate in 30 mL of 1.5×SSPE, 0.5% SDS containing 90 µl SA-HRP, for 10 minutes at 50° C. in a shaking water bath (70 rpm). Rinse: Briefly rinse in 1.5×SSPE, 0.5% SDS.
4. Wash: Incubate in 150 mL of 1.5×SSPE, 0.5% SDS at room temperature for 15 minutes on an orbital shaker (100 –125 rpm). Rinse: Briefly rinse in approximately 150 mL of 0.1M NaCitrate, pH 5.
5. ECL: Add 10 mL ECL reagent A to 10 mL ECL reagent B. Shake the membrane in the ECL reagents for exactly 1 minute at room temperature.
6. Expose Film: Place the membrane on the plastic side of benchkote and place Saran Wrap over the membrane. Use a paper towel to smooth out any wrinkles in the Saran Wrap. Expose to Hyperfilm or Kodak XAR5 film for 15 minutes.

---

We claim:

1. A labeled or unlabeled oligonucleotide probe, wherein said oligonucleotide probe sequence consists of Seq ID No. 1 or the complement thereto.

2. An oligonucleotide probe of claim 5 selected from the group consisting of probes SW49, SW1000, SW1001, SW1002, SW1003, SW1004, and SW1005, which probes each have the nucleotide sequence of SEQ ID No. 1 and which probes each consist of a different label moiety.

3. A kit for quantitating the amount of human DNA in a sample said kit comprising an oligonucleotide probe of claim 1.

4. A biotin labeled oligonucleotide probe according to claim 1.

* * * * *

UNITED STATES PATENT AND TRADEMARK OFFICE
CERTIFICATE OF CORRECTION

PATENT NO. : 5,464,945
DATED : November 7, 1995
INVENTOR(S) : Rebecca Reynolds and P. Sean Walsh It is certified that error appears in the above-indentified patent and that said Letters Patent is hereby corrected as shown below:

In column 21, Claim 2, line 1, please delete "5" and insert therefor --1--.

In column 22, Claim 3, line 2, after "sample" please insert --,--.

Signed and Sealed this

Nineteenth Day of March, 1996

Attest:

BRUCE LEHMAN

Attesting Officer    Commissioner of Patents and Trademarks